(12) United States Patent
Seo et al.

(10) Patent No.: US 10,018,568 B2
(45) Date of Patent: Jul. 10, 2018

(54) DEVICE FOR MONITORING BIOFILM

(71) Applicant: KOREA UNIVERSITY RESEARCH AND BUSINESS FOUNDATION, SEJONG CAMPUS, Sejong-si (KR)

(72) Inventors: Sung-Kyu Seo, Gyeonggi-Do (KR); Un-Hwan Ha, Daejeon (KR)

(73) Assignee: KOREA UNIVERSITY RESEARCH AND BUSINESS FOUNDATION, SEJONG CAMPUS, Sejong-Si (KR)

( * ) Notice: Subject to any disclaimer, the term of this patent is extended or adjusted under 35 U.S.C. 154(b) by 246 days.

(21) Appl. No.: 14/650,056

(22) PCT Filed: Nov. 25, 2013

(86) PCT No.: PCT/KR2013/010730
§ 371 (c)(1),
(2) Date: Jun. 5, 2015

(87) PCT Pub. No.: WO2014/088249
PCT Pub. Date: Jun. 12, 2014

(65) Prior Publication Data
US 2015/0338350 A1    Nov. 26, 2015

(30) Foreign Application Priority Data
Dec. 6, 2012   (KR) .................. 10-2012-0141036

(51) Int. Cl.
C12M 1/00    (2006.01)
G01N 21/00   (2006.01)
(Continued)

(52) U.S. Cl.
CPC ......... *G01N 21/8422* (2013.01); *G01N 21/00* (2013.01); *G01N 33/4875* (2013.01); *G01N 33/48785* (2013.01); *G01N 2201/061* (2013.01)

(58) Field of Classification Search
CPC ...... C12M 25/14; C12M 25/02; C12M 25/06; G01N 21/00; G01N 21/8422
See application file for complete search history.

(56) References Cited

U.S. PATENT DOCUMENTS 4,939,151 A * 7/1990 Bacehowski .......... C12M 23/08
                                                    206/484.1
5,459,069 A * 10/1995 Palsson .............. C07K 14/5403
                                                    435/289.1
(Continued)

FOREIGN PATENT DOCUMENTS

JP    2007-525216 A    9/2007
JP    2011-067772 A    4/2011
(Continued)

*Primary Examiner* — Nathan A Bowers
(74) *Attorney, Agent, or Firm* — Hauptman Ham, LLP (57) ABSTRACT

The present invention relates to a device for monitoring a biofilm, which can monitor a formation state of the biofilm by using a biofilm shadow image. According to one embodiment of the present invention, the device for monitoring a biofilm can comprise: a water tank for storing water; a monitoring substrate arranged inside the water tank and surface-treated so as to accelerate the biofilm formation; a light-emitting module located at an upper portion of the monitoring substrate so as to emit light in a monitoring substrate direction; and an image sensor unit arranged below the monitoring substrate so as to capture a shadow image of the biofilm, which is formed on the monitoring substrate.

12 Claims, 8 Drawing Sheets

(51) Int. Cl.
*G01N 33/00* (2006.01)
*G01N 21/84* (2006.01)
*G01N 33/487* (2006.01)

(56) References Cited

U.S. PATENT DOCUMENTS

| | | | | |
|---|---|---|---|---|
| 5,858,769 | A * | 1/1999 | DiGuiseppi | C12M 23/08 435/286.2 |
| 2002/0068312 | A1 * | 6/2002 | Castellini | G01N 17/008 435/29 |
| 2003/0012688 | A1 * | 1/2003 | Kippenhan, Jr. | A61L 2/18 422/28 |
| 2004/0086956 | A1 * | 5/2004 | Bachur, Jr. | G01N 21/171 435/34 |
| 2010/0035337 | A1 * | 2/2010 | Bahnemann | C12M 23/22 435/292.1 |
| 2013/0034842 | A1 * | 2/2013 | Tunheim | G01N 21/85 435/3 |
| 2015/0232797 | A1 * | 8/2015 | Kasuto | C12M 23/34 435/395 |

FOREIGN PATENT DOCUMENTS

| | | |
|---|---|---|
| KR | 10-2005-0007540 A | 1/2005 |
| KR | 10-2011-0006248 A | 1/2011 |

* cited by examiner

DEVICE FOR MONITORING BIOFILM

TECHNICAL FIELD

The present invention relates to a device for monitoring a biofilm, and more particularly, to a device for monitoring a biofilm, which can monitor a formation state of the biofilm by using a shadow image of the biofilm.

BACKGROUND ART

Biofilms are biological films which are produced as specific bacteria are proliferated on specific surfaces through processes of adsorption, growth, and desorption. Traditionally, techniques for measuring the biofilms are as follows.

Enzyme-linked immunosorbent assay (ELISA) is a technique of measuring absorbance, light emission, or fluorescence by selectively reacting only cells in a specific state, using an antibody having high singularity and high sensitivity and an enzyme serving as a signal generating source.

Photospectrometry is a technique in which bacteria that become the source of a biofilm are dyed with a specific kind of reagent, and the dyed sample is dissolved with a solvent such as alcohol, so that the concentration of the reagent used in the dyeing of the bacteria is detected by measuring an absorbance at a specific wavelength.

In the above-described methods, high-priced exclusive equipments such as an ELISA reader and a photospectrometer are used, and therefore, a large amount of cost and a complicated system are required. Also, in these methods, cells should always be marked with an additional material such as a specific dye reagent or enzyme, and hence a separate reagent is necessarily required. Therefore, the methods are not suitable for real-time monitoring in which the formation of a biofilm can be continuously monitored.

Korean Patent Publication No. 10-2005-0007540 discloses a method for automatically measuring the formation of a microorganism biofilm by using a confocal imaging system and a method for measuring effects of the revelation of microorganism genes in a test chemical and the formation of a biofilm.

However, in Korean Patent Publication No. 10-2005-0007540, a separate reagent is necessarily required to measure a formation state of the biofilm, and therefore, the method is not suitable for real-time monitoring in which the formation of the biofilm can be continuously monitored.

Accordingly, studies on a real-time monitoring device and an analysis method of a biofilm are required, which are more simple and inexpensive, require no separate reagent, and do not destroy samples.

SUMMARY OF THE DISCLOSURE

An embodiment of the present invention is directed to a device for monitoring a biofilm, which can accelerate the formation of a biofilm existing in water and monitor a formation state of the biofilm by using a shadow image of the biofilm.

According to an aspect of the present invention, there is provided a device for monitoring a biofilm, the device including: a water tank for storing water; a monitoring substrate disposed inside the water tank, the monitoring substrate being surface-treated to accelerate the formation of a biofilm; a light-emitting module located above the monitoring substrate to emit light in the direction of the monitoring substrate; and an image sensor unit disposed under the monitoring substrate to capture a shadow image of the biofilm, formed on the monitoring substrate.

It should be understood that different embodiments of the invention, including those described under different aspects of the invention, are meant to be generally applicable to all aspects of the invention. Any embodiment may be combined with any other embodiment unless inappropriate. All examples are illustrative and non-limiting.

In the device according to the present invention, it is possible to continuously observe the formation state of a biofilm without any separate reagent while using a simple and low-priced device.

Further, it is possible to automate, with the development of computer software combined with a simple image processing technique, information that was acquired only using various types of measuring equipments such as an enzyme-linked immunosorbent assay (ELISA) reader and a photospectrometer through processes in which skilled inspectors or engineers collect samples and perform separate dyeing or attachment of an identifier. Thus, it is possible to decrease cost and remarkably reduce measurement errors.

Further, pixel values of shadow images of biofilms formed by bacteria are used, so that it is possible to easily analyze formation degrees of biofilms without any high-priced device.

DETAILED DESCRIPTION

Hereinafter, a device for monitoring a biofilm and a method of analyzing a formation state of a biofilm by using the device according to an embodiment of the present invention will be described with reference to the accompanying drawings.

As used herein, the singular terms are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence and/or addition of one or more other features, integers, steps, operations, elements, components, and/or groups thereof.

A device for monitoring a biofilm according to an embodiment of the present invention can accelerate the formation of a biofilm existing in water and monitor a formation state of the biofilm by using a shadow image of the biofilm.

A biofilm is a biological film which is produced as specific bacteria are proliferated on a specific surface through processes of adsorption, growth, and desorption. That is, the biofilm is an assembly of bacteria, and has a form in which the assembly of bacteria is thinly adhered like a film. The biofilm is produced due to bacteria. However, the biofilm may again provide a habitat to the bacteria and become a factor that the proliferation of the bacteria is accelerated.

A device for monitoring a biofilm according to an embodiment of the present invention may include a configuration in which a sensor for capturing a shadow image of a biofilm exists outside a water tank and a configuration in which a sensor for capturing a shadow image of a biofilm exists inside a water tank.

A device for monitoring a biofilm according to an embodiment of the present invention may be implemented as a device for supplying water. For example, the device may include a wafer purifier, a water dispenser (including a chiller/heater), and the like.

Figure 1:
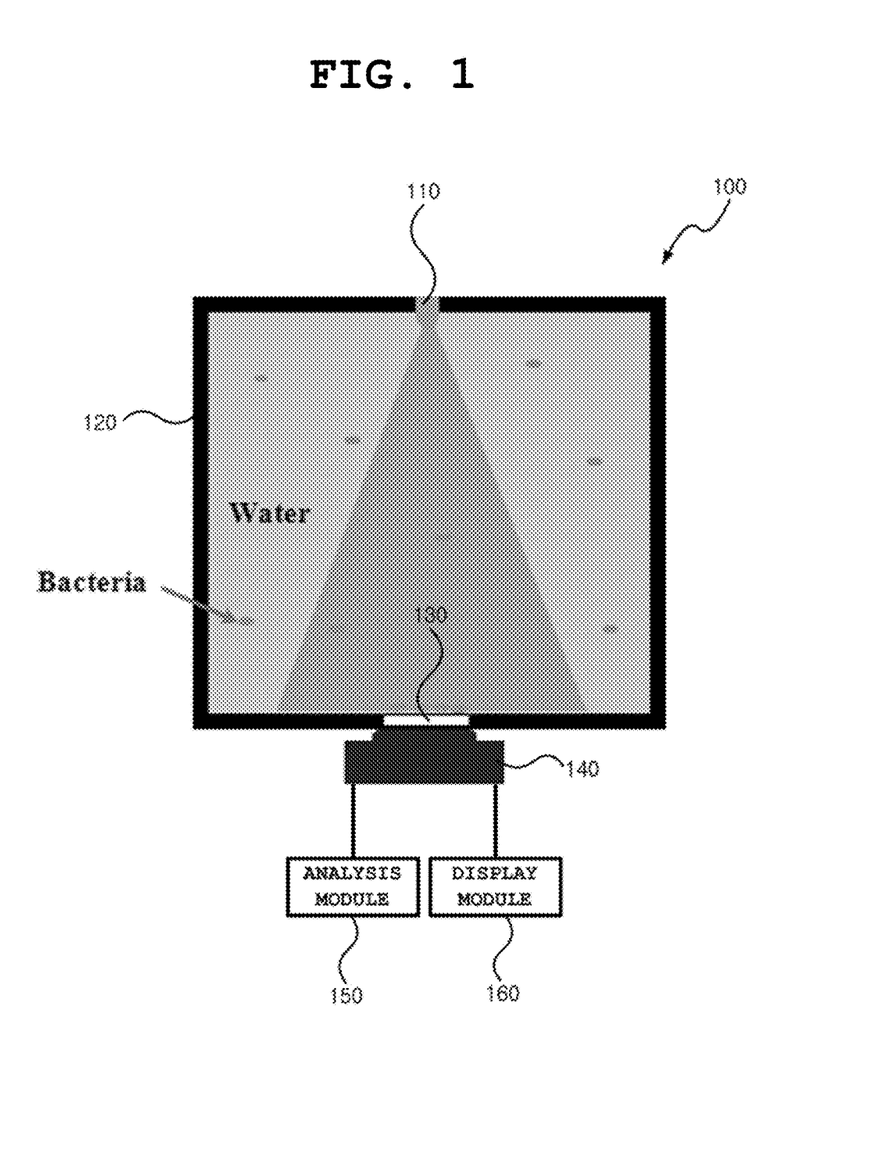
FIGS. 1 and 2 illustrate devices for monitoring biofilms according to embodiments of the present invention.

FIG. 1 illustrates a device for monitoring a biofilm according to an embodiment of the present invention. The device has a configuration in which a sensor for capturing a shadow image exists outside a water tank.

As shown in this figure, the device 100 may include a light-emitting module 110, a water tank 120, a monitoring substrate 130, a sensor unit 140, an analysis module 150, and a display module 160.

The light-emitting module 110 emits light to capture a shadow image of a biofilm. For example, the light-emitting module 110 may be implemented in the form of an ultraviolet lamp (UV lamp) located at an upper end of the water tank 120. The UV lamp has an advantage of showing a sterilization effect.

Water may be stored in the water tank 120. Bacteria may be included in the water stored in the water tank 120.

The monitoring substrate 130 may be formed at a predetermined portion of the bottom surface inside the water tank 120. A surface contacted with the water in the monitoring substrate 130 may be surface-treated so as to accelerate the formation of the biofilm. A method for performing surface treatment to accelerate the formation of a biofilm will be described later.

In this specification, that the formation of a biofilm is accelerated does not mean that a biofilm is formed by producing bacteria that have not existed but means that the formation of a biofilm is accelerated by gathering bacteria that have been already scattered in water concentratedly at a specific location (e.g., the surface-treated monitoring substrate).

The monitoring substrate 130 may be made of at least one material of glass, plastic, and polymer. The monitoring substrate 130 may be optically transparent. When the monitoring substrate 130 is transparent, the shadow image of a biofilm formed on the monitoring substrate 130 can be more accurately captured. The monitoring substrate 130 may be contacted with an upper end of the sensor unit 140 to be attachable/detachable to/from the sensor unit 140. Thus, when the monitoring substrate 130 is not transparent due to a large amount of foreign matter or biofilm formed on the monitoring substrate 130, only the monitoring substrate 130 can be replaced to be attached to the sensor unit 140.

The sensor unit 140 may be disposed under the monitoring substrate 130. The sensor unit 140 may include an image sensor which can capture shadow images of a biofilm. The image sensor may be implemented as a complementary metal-oxide semiconductor (CMOS) image sensor. The CMOS image sensor is a low power consumption type image capture device having a CMOS structure. The image sensor may be implemented in a form having no lens. The CMOS image sensor can be mass-produced through a semiconductor process. Hence, the CMOS image sensor has low price and high processing speed. The image sensor has a wide observation range and can perform a quantitative and automated analysis, as compared with a microscope or enzyme-linked immunosorbent assay (ELISA) reader.

The device 100 shown in FIG. 1 has a structure in which the monitoring substrate 130 is disposed inside the water tank 120, and the sensor unit 140 is disposed outside the water tank 120.

The analysis module 150 performs a function of analyzing the shadow image of the biofilm, captured by the sensor unit 140, through an image processing technique. The analysis module 150 may analyze a formation degree of the biofilm by extracting, from the captured shadow image of the biofilm, at least one of a signal-to-noise ratio (SNR), a pixel-value variation (PV), a maximum intensity (MAX), a minimum intensity (MIN), and an averaged intensity (AVE). The MAX means a maximum pixel value, the MIN means a minimum pixel value, and the AVE means an average of pixel values.

The analysis module 150 shown in this figure may be implemented as one component of the device 100. However, the analysis module 150 may also be implemented as a separate device from the device 100.

When the analysis module 150 exists separately from the device 100, the analysis module 150 may receive the shadow image of the biofilm from the sensor unit 140 through various communication manners (e.g., wire/wireless communications).

The display module 160 may display a result (e.g., a formation state of the biofilm) analyzed through the analysis module 150. When the formation degree of the biofilm exceeds a critical value, the display module 160 may output a warning signal. In the embodiment shown in this figure, the display module 160 is implemented separately from the analysis module 150. However, the display module 160 may be implemented as one component of the analysis module 150.

Figure 2:
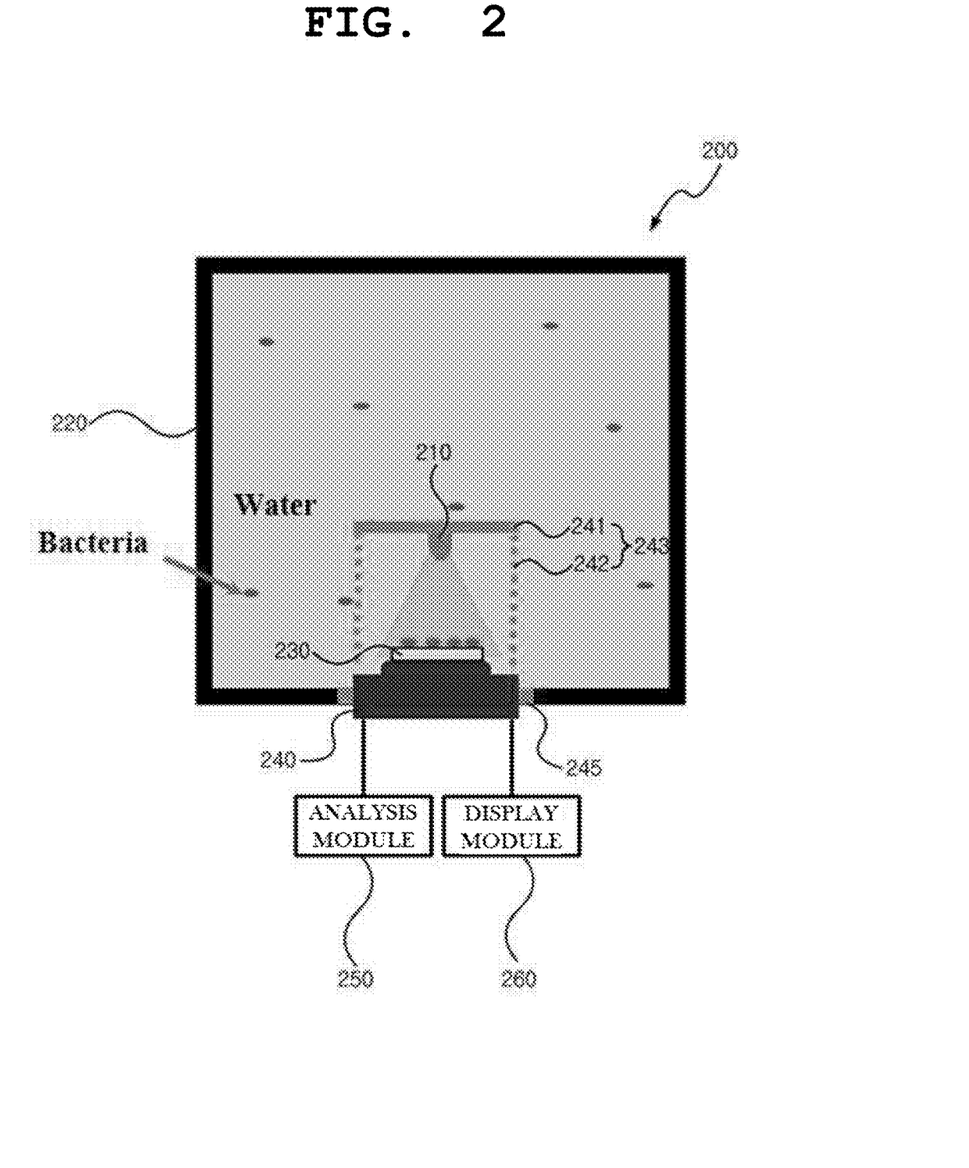

FIG. 2 illustrates a device for monitoring a biofilm according to the embodiment of the present invention. The device has a configuration in which a sensor for capturing a shadow image exists inside a water tank.

As shown in this figure, the device 200 may include a light-emitting module 210, a water tank 220, a monitoring substrate 230, a sensor unit 240, an analysis module 250, and a display unit 260.

Functions performed in the light-emitting module 210, the water tank 220, the monitoring substrate 230, the sensor unit 240, the analysis module 250, and the display module 260 may be identically applied to the components shown in FIG. 1. Here, detailed description of the function of each component is omitted, and its structure will be described.

The sensor unit 240 may be attachably/detachably provided inside the water tank 220. Sealing members 245 laterally formed at a lower end portion of the sensor unit 240 may be respectively formed at both sides of the sensor unit 240 to be inserted into a groove formed in the bottom surface inside the water tank 220.

The sensor unit 240 may be provided with a housing 243 to be integrated with the light-emitting module 210. The housing 243 may include an upper substrate 241 having a space in which the light-emitting module 210 can be fixed and sidewalls 242 which are connected to the upper substrate 241 and formed such that water can pass therethrough.

Thus, in the device 200, the sensor unit 240, the light-emitting module 210, and the monitoring substrate 230 can be integrally formed. Accordingly, when any one of the sensor unit 240, the light-emitting module 210, and the monitoring substrate 230 is replaced, the sensor unit 240, the light-emitting module 210, and the monitoring substrate 230, which are integrally formed, can be replaced as one set.

Meanwhile, in the device 100 or 200 according to the embodiment of the present invention, in addition to the UV lamp, an RGB light-emitting diode (LED) may be used for the light-emitting module 110 or 210 to capture a clear shadow image.

Figure 3:
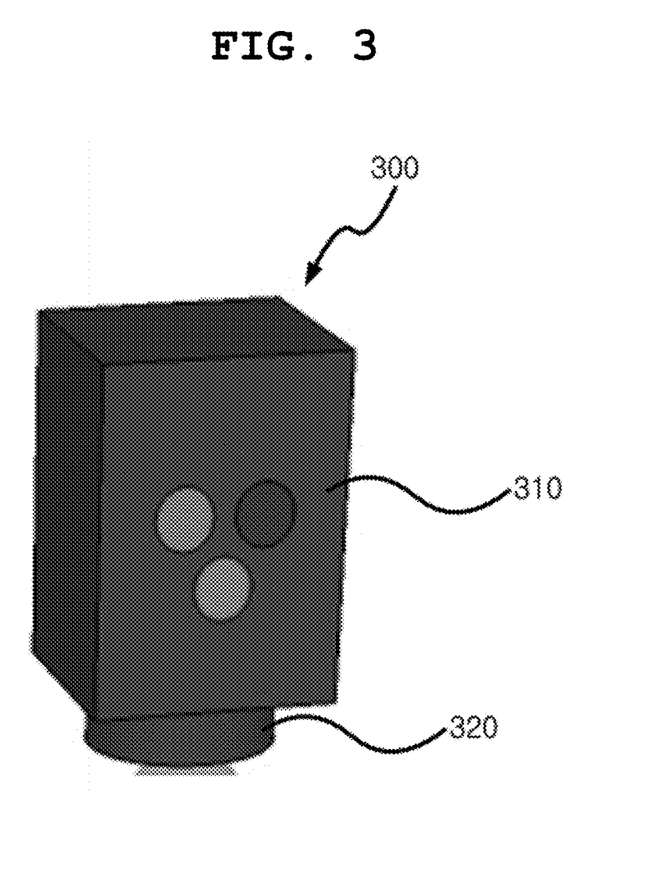
FIG. 3 illustrates a light-emitting module to be provided in a device for monitoring a biofilm according to an embodiment of the present invention.

FIG. 3 illustrates a light-emitting module to be provided in a device for monitoring a biofilm according to an embodiment of the present invention.

The light-emitting module 300 shown in this figure may include an RGB LED 310 and a pinhole 320. When the RGB LED 310 is used for the light-emitting module 300, a clear shadow image can be captured with respect to a specific color.

The pinhole 320 may be coupled to a lower end of the RGB LED 310 to clear shadow images of biofilms. That is, the pinhole 320 may be used to increase the optical coherence and illumination intensity of light.

The pinhole 320 may be manufactured in the form of a film mask made of a plastic material. A film mask pinhole made of a plastic material may be output on an OHP film or the like by using a high-resolution laser printer and then attached to the front of the RGB LED 110. Thus, the film mask pinhole can be easily manufactured at a remarkably low cost, as compared with a general pinhole made of plastic or metal material. In the case of a multi-wavelength light source, like the RGB LED, in which individual light sources of three colors (red, green, and blue) are integrated in one LED, three pinholes are to be located at a distance of a few tens of micrometers. If a method of outputting pinholes by using a high-resolution laser printer is used, multiple pinholes can be easily designed on a computer.

Figure 4:
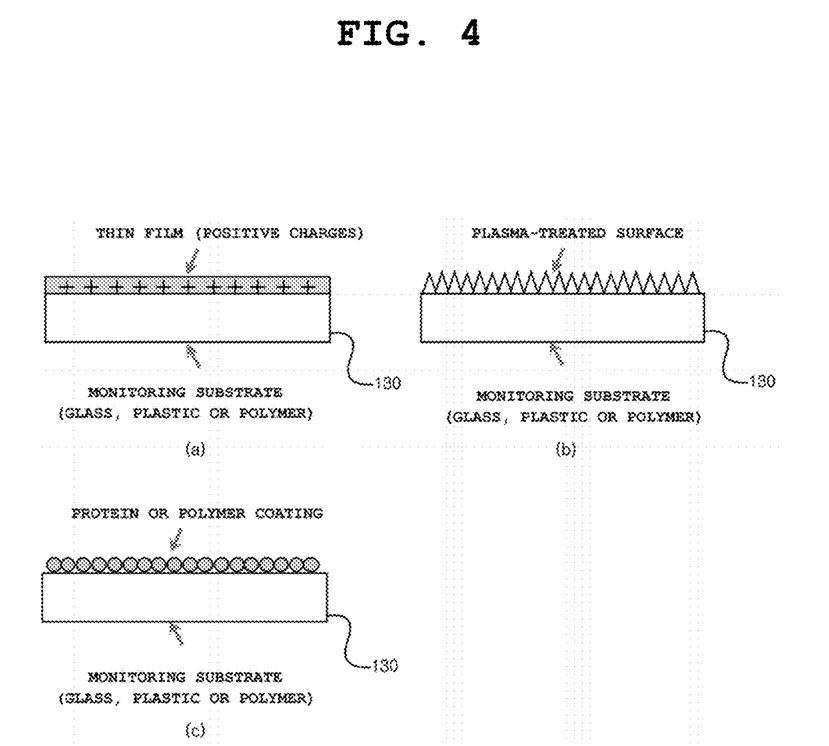
FIG. 4 is a view illustrating a monitoring substrate that is one component of a device for monitoring a biofilm according to an embodiment of the present invention.

FIG. 4 is a view illustrating a monitoring substrate that is one component of a device for monitoring a biofilm according to an embodiment of the present invention. Particularly, a method of performing surface treatment to accelerate the formation of a biofilm on the monitoring substrate 130 or 230 will be described. The monitoring substrate 130 shown in FIG. 1 will be described as an example.

FIG. 4(*a*) illustrates an example in which a monitoring substrate charged with positive charges is used to accelerate the formation of a biofilm.

Generally, it is known that bacteria have net negative charges on walls of cells in a neutral pH. The charges determine a zeta-potential. In this case, most bacteria have a negative zeta-potential in a physiological pH (pH7). Particularly, it is known that lipopolysaccharides existing in walls of cells of gram-negative bacteria have a high affinity to positive charges. Thus, in an embodiment of the present invention, a thin film made of titanium oxide ($TiO_2$), aluminum oxide ($Al_2O_3$), or iron oxide ($Fe_2O_3$) of a thickness of a few nm to a few hundreds nm, which generally has positive charges, is formed on the monitoring substrate 130 to take charge of adsorbing bacteria, thereby accelerating the adsorption of bacteria.

FIG. 4(*b*) illustrates an example in which a monitoring substrate reformed with a hydrophobic surface is used to accelerate the formation of a biofilm.

Hydrophobicity plays an important role in the adsorption of bacteria. For example, spores of bacteria are well adhered to surfaces due to the hydrophobicity, or colon bacilli are well adhered to activated sludge flocs due to the hydrophobicity. This shows how important role the hydrophobicity of surfaces of bacteria plays in the adsorption of the bacteria. The hydrophobicity of the surfaces of the bacteria is determined according to kinds of protein molecules existing in the bacteria. If a proteolytic enzyme such as trypsin is processed by bacteria, the hydrophobicity of pathogenic bacteria such as *vibrio proteolytica* or *streptococcus sanguis* decreases, and therefore, the adsorption rate of bacteria with respect to a hydrophobic surface such as polystyrene or hexadecane decreases. Accordingly, in an embodiment of the present invention, a method for accelerating the formation of a biofilm by performing oxygen plasma treatment on a substrate made of glass, plastic, or transparent polymer material to increase the hydrophobicity of the substrate may be used to increase the hydrophobicity of the surface of the monitoring substrate 130.

FIG. 4(*c*) illustrates an example in which a monitoring substrate coated with a protein or polymer is used to accelerate the formation of a biofilm.

A method of coating surfaces with an organic material such as a protein is used as a treatment for increasing the adsorption of bacteria. The coating has influence on physical and chemical properties of a surface by changing the free energy, hydrophobicity, and electrostatic charges of the surface. Accordingly, in an embodiment of the present invention, a method may be used which accelerates the formation of a biofilm by coating the monitoring substrate 130 with a protein such as bovine serum albumin (BSA) or a polymer such as polydimethylsiloxane (PDMS).

Figure 5:
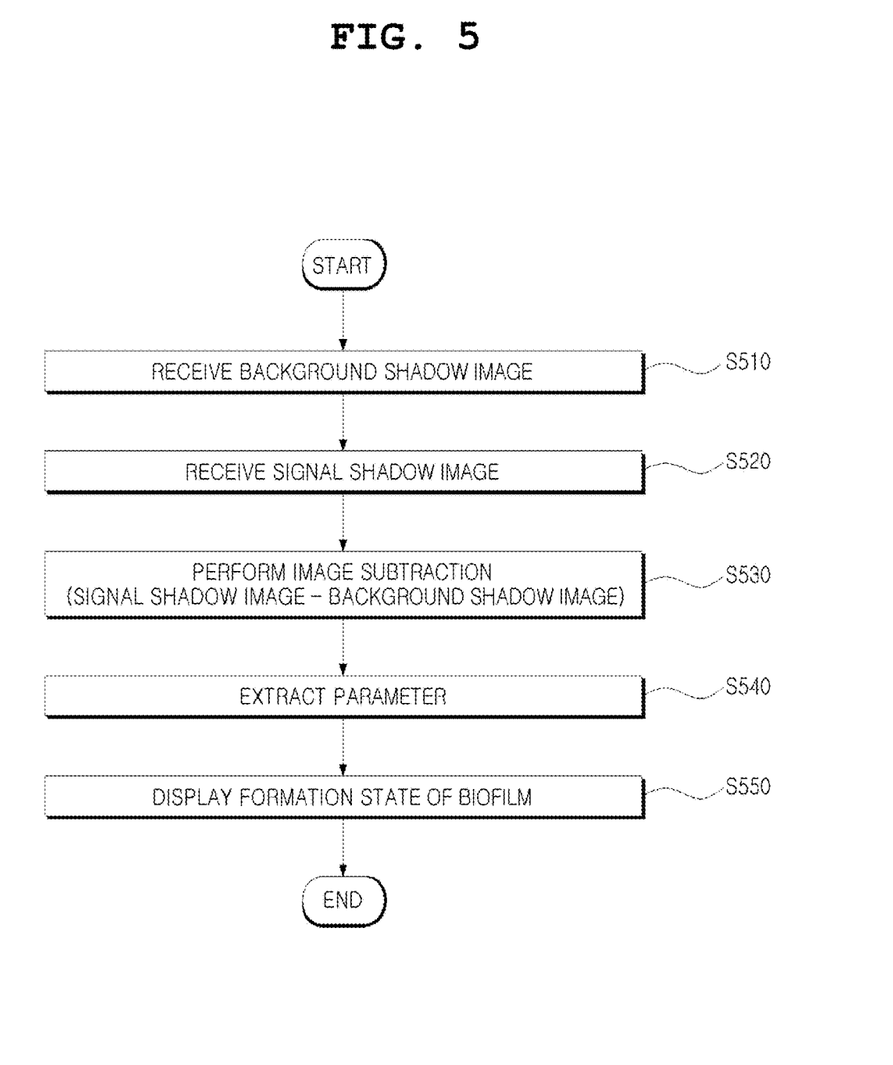
FIG. 5 is a flowchart illustrating a method for monitoring a biofilm by using a device for monitoring a biofilm according to an embodiment of the present invention.

FIG. 5 is a flowchart illustrating a method for monitoring a biofilm by using a device for monitoring a biofilm according to an embodiment of the present invention. That is, FIG. 5 illustrates a process for analyzing a formation degree of a biofilm by using a captured shadow image of the biofilm. The analysis process may be performed in the analysis module 150 or 250.

The formation of a biofilm generally takes a long period of a few hours to a few days. Therefore, a background shadow image is captured at a point of time when measurement starts, and then, if the formation of a biofilm starts, a signal shadow image is captured at a point of time when a user desires the measurement (S510 and S520). Subsequently, noise on the background shadow image may be effectively removed through an image subtraction technique (S530). A specific parameter may be extracted from each pixel value through an image analysis technique (S540). The specific parameter may include at least one of a signal-to-noise ratio (SNR), a pixel-value variation (PV), a maximum intensity (MAX), a minimum intensity (MIN), and an averaged intensity (AVE).

The extracted parameter is displayed to indicate a formation degree of the biofilm, thereby completing the analysis process (S550).

The SNR may be expressed as Equation 1.

$$SNR = 20 \log|(Max(I) - \mu_b)/\sigma_b| \quad \text{Equation 1}$$

Here, $\mu_b$ and $\sigma_b$ denote an average value and a standard deviation of the shadow images, respectively, and Max(I) denotes a maximum brightness pixel value.

The PV may be expressed as Equation 2.

$$PV = \sqrt{\frac{1}{N}\sum_{i=1}^{N}(x_i - \mu)^2} \quad \text{Equation 2}$$

Here, N denotes a number of total pixels, xi denotes a brightness value in a specific pixel, and μ denotes a brightness average value of N pixels.

Among pixel values constituting the shadow images, the MAX means a maximum brightness pixel value, the MIN means a minimum brightness pixel value, and the AVE means an average brightness pixel value.

Hereinafter, results obtained through the above-described analysis process will be described.

Figure 6:
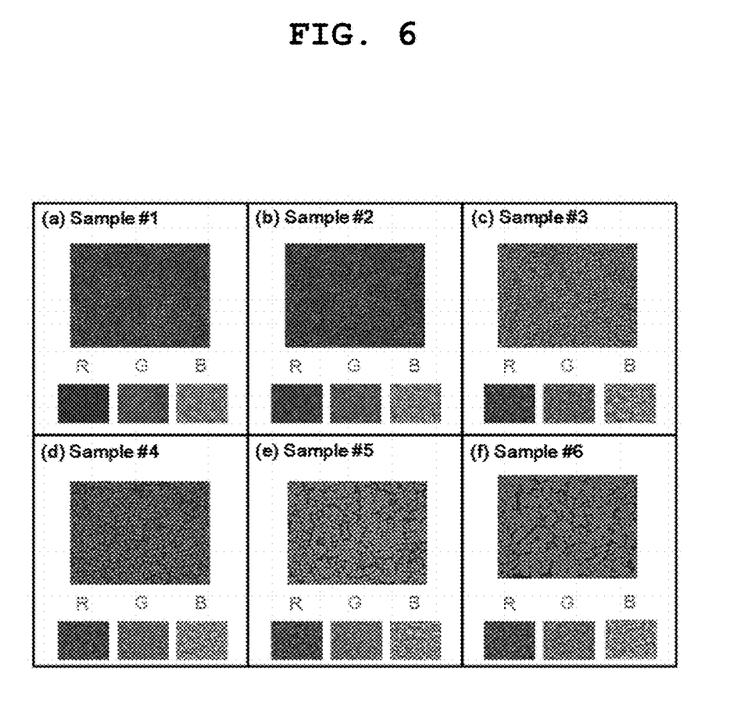
FIG. 6 is a view comparing biofilm images captured using a device for monitoring a biofilm according to an embodiment of the present invention with biofilm images captured using a microscope.

FIG. 6 is a view comparing biofilm images captured using a device for monitoring a biofilm according to an embodiment of the present invention with biofilm images captured using a microscope.

FIG. 6 is a view comparing images of a biofilm according to change in concentration of a supernatant (sup) for accelerating the revelation of 5309mt as a kind of bacterium participating in the formation of the biofilm. The concentration of the supernatant (sup) means the concentration of the supernatant as an inducing factor used to accelerate the formation of a biofilm. The supernatant may be construed as a floating matter or supernatant liquid. In this embodiment, an element for accelerating the formation of a biofilm is injected in the form of a supernatant liquid, and a change in the formation degree of the biofilm is observed depending on a concentration of the element.

For the concentration of the supernatant (sup) used in FIG. 6, the concentration of Sample #1 is 1250 μM, the concentration of Sample #2 is 1000 μM, the concentration of Sample #3 is 750 μM, the concentration of Sample #4 is 500 μM, the concentration of Sample #5 is 250 μM, and the concentration of Sample #6 is 0 μM.

The concentration of sup is highest in Sample #1, and gradually decreases as the number of Sample increases. FIG. 6 is a view illustrating shadow images (lower end) of respective biofilms captured under the irradiation of LEDs having red (R), green (G), and blue (B) wavelengths through the device and images (upper end) of cells captured through the microscope through a separate dyeing process. As shown in this figure, biofilms which could be observed using only the microscope through the separate dyeing process or detected using only the ELISA reader or the like can be monitored in real time without any separate dyeing process or reagent through a monitoring device configured with only compact photoelectron components. In this embodiment, the device shown in FIG. 1 was used.

Figure 7:
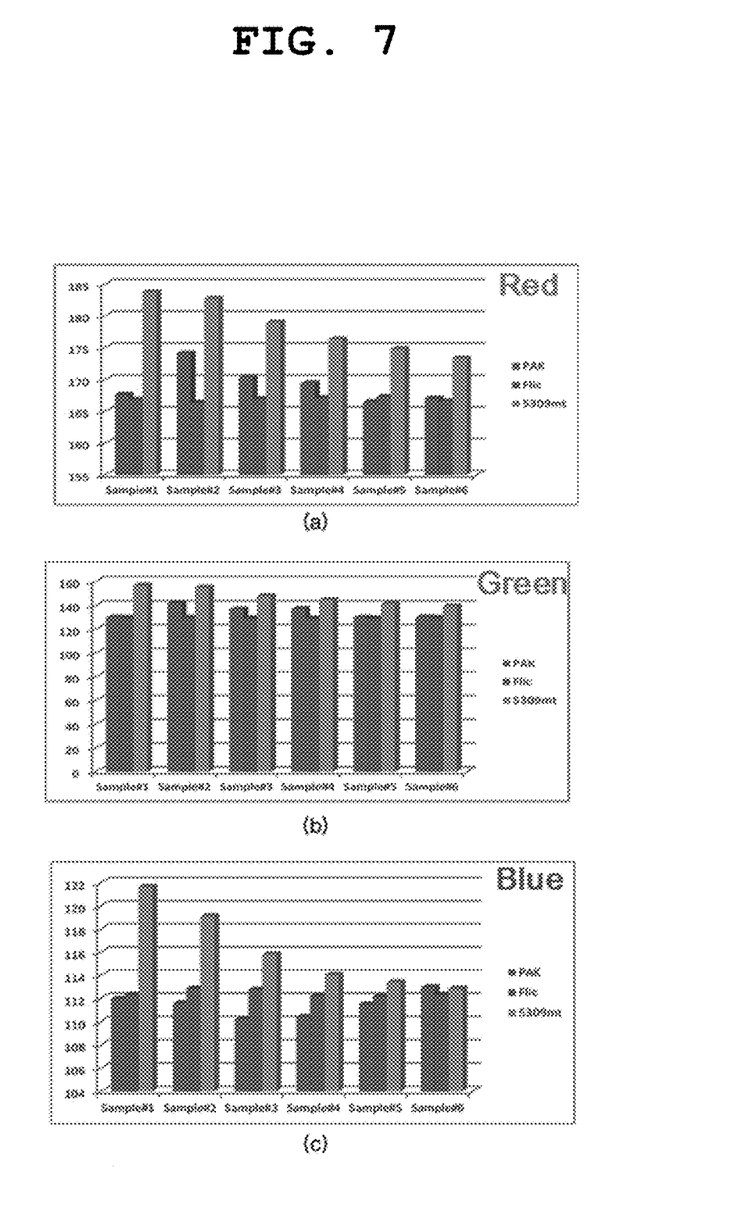
FIG. 7 illustrates results obtained by comparing shadow images of biofilms formed by PAK, Flic, and 5309mt as kinds of bacteria, which are measured using a device for monitoring a biofilm according to an embodiment of the present invention.

FIG. 7 illustrates results obtained by comparing shadow images of biofilms formed by PAK, Flic, and 5309mt as kinds of bacteria, which are measured using a device for monitoring a biofilm according to an embodiment of the present invention. For the concentration of the supernatant (sup) used in FIG. 7, the concentration of Sample #1 is 1250 μM, the concentration of Sample #2 is 1000 μM, the concentration of Sample #3 is 750 μM, the concentration of Sample #4 is 500 μM, the concentration of Sample #5 is 250 μM, and the concentration of Sample #6 is 0 μM.

FIG. 7 illustrates results obtained by comparing shadow images of biofilms formed by PAK and Flic which are kinds of bacteria known that they hardly cause the formation of biofilms, and 5309mt which is a kind of bacterium actively forming biofilms in the device 100 shown in FIG. 1. Here, the light-emitting module 300 including the RGB LED 310 and the pinhole 320 was used as a light-emitting module.

The results obtained by analyzing the shadow images of the respective biofilms captured under the irradiation of the LEDs having the red (R), green (G), and blue (B) wavelengths show a tendency that the formation degree of the biofilm gradually decreases according to concentrations of sup in experiments using 5309mt, and the difference between signals is greatest under the irradiation of the LED having the blue (B) wavelength. In the case of another kind of bacterium rather than 5309mt actively forming biofilms, the irradiation of light having various wavelengths may be advantageous to detect formation degrees of a biofilm, and hence the RGB LED having various wavelengths was used as a light source. However, the UV lamp having the wavelength of light that sterilizes bacteria in a water tank may also be used as a light source according to application fields.

Figure 8:
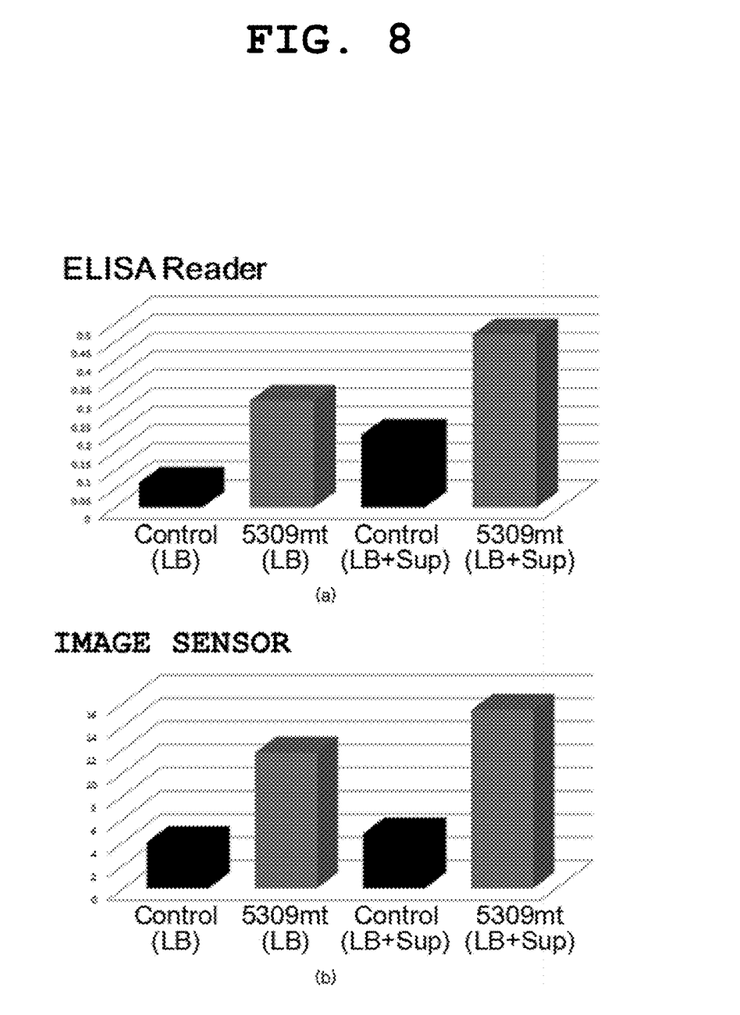
FIG. 8 is a view comparing results obtained by measuring biofilms formed by PAK and 5309mt as kinds of bacteria, using a device for monitoring a biofilm according to an embodiment of the present invention and a traditional enzyme-linked immunosorbent assay (ELISA) reader.

FIG. 8 is a view comparing results obtained by measuring biofilms formed by PAK and 5309mt as kinds of bacteria, using a device for monitoring a biofilm according to an embodiment of the present invention and a traditional ELISA reader. The concentration of sup shown in FIG. 8 is 1250 μM.

FIG. 8 is a view comparing formation degrees of biofilms formed by PAK which is a bacterium known that it hardly causes the formation of biofilms and a bacterium (5309mt) actively forming biofilms in a measurement method using the traditional ELISA reader and a measurement method (using the device shown in FIG. 1) according to an embodiment of the present invention. Through the measurement using the traditional ELISA reader, it can be seen that the formation of biofilms by both PAK and 5309 in a biofilm formation accelerator (sup) is accelerated as compared with that in a culture fluid. Also, it can be seen that although the same sample is measured in the method according to the embodiment of the present invention, a similar result is obtained.

Thus, the method according to the embodiment of the present invention is used, so that it is possible to continuously observe the formation of a biofilm without any separate reagent while using a simple and low-priced device such as a CMOS image sensor or LED rather than a traditional biofilm measurement method or high-priced equipment.

The above-described method of analyzing the formation state of the biofilm may be implemented in a program command form capable of being performed through various computer means to be recorded in a computer-readable recording medium. The computer-readable recording medium may include a program command, a data file, a data structure, and the like separately or in a combination thereof. The program command recorded in the recording medium may be a command designed or configured specially for the present invention, or usably known to a person having ordinary skill in the computer software art.

The computer-readable recording medium includes magnetic media such as hard disks, floppy disks and magnetic tapes, optical media such as a CD-ROM and a DVD, magneto-optical media such as floptical disks, and hardware devices such as a ROM, a RAM and a flash memory, which are specially configured to store and perform program commands.

Meanwhile, the recording medium may be a transmission medium such as an optical or metallic line or a waveguide, including a carrier for transmitting signals to indicate program instructions, a data structure, etc.

Further, the program commands include a machine language code generated by a compiler and a high-level language code executable by a computer through an interpreter and the like. The hardware devices can be configured as at least one software module to perform the operation of embodiments of the present invention, and vice versa.

While the present invention has been described with respect to the specific embodiments, it will be apparent to those skilled in the art that various changes and modifications may be made without departing from the spirit and scope of the invention as defined in the following claims.

The invention claimed is:

1. A device for monitoring a biofilm, the device comprising:
    a water tank configured to store water;
    a transparent monitoring substrate coated with a protein in order to form a biofilm on the transparent monitoring substrate, and disposed inside the water tank;
    a light-emitting module located above the transparent monitoring substrate, and configured to emit light in the direction of the transparent monitoring substrate;
    an image sensor unit disposed under the transparent monitoring substrate, and configured to capture a shadow image of the biofilm formed on the transparent monitoring substrate; and
    a housing including
        an upper substrate to which the light-emitting module is fixed,
        sidewalls formed such that water is to pass therethrough, connected to the upper substrate, and configured to contain the transparent monitoring substrate, and
        a bottom substrate, where the image sensor unit is fixed, opposite to the upper substrate, and connected to the sidewalls,
    wherein the image sensor unit, the transparent monitoring substrate, and the light-emitting module are integrally formed.

2. The device of claim 1, wherein the transparent monitoring substrate is made of at least one material of glass, plastic, and polymer.

3. The device of claim 1, wherein the light-emitting module includes at least one of an RGB light emitting diode having a pinhole provided at a lower end thereof and an ultraviolet lamp.

4. The device of claim 1, wherein the sensor unit is disposed outside the water tank, to be contacted with the transparent monitoring substrate.

5. The device of claim 4, wherein the transparent monitoring substrate is attachably/detachably contacted with the sensor unit.

6. The device of claim 5, further comprising an analysis module for analyzing a formation state of the biofilm by extracting a specific parameter from the shadow image of the biofilm captured through the sensor unit.

7. The device of claim 6, wherein the specific parameter includes at least one of a signal-to-noise ratio (SNR), a pixel-value variation (PV), a maximum intensity (MAX), a minimum intensity (MIN), and an averaged intensity (AVE) of the shadow image.

8. The device of claim 1, wherein the sensor unit is disposed inside the water tank, to be contacted with the transparent monitoring substrate.

9. The device of claim 1, wherein the sensor unit further includes a sealing member to be inserted into a groove formed inside the water tank, to be attachable/detachable to/from the water tank.

10. The device of claim 9, further comprising an analysis module for analyzing a formation state of the biofilm by extracting a specific parameter from the shadow image of the biofilm captured through the sensor unit.

11. The device of claim 10, wherein the specific parameter includes at least one of a signal-to-noise ratio (SNR), a pixel-value variation (PV), a maximum intensity (MAX), a minimum intensity (MIN), and an averaged intensity (AVE) of the shadow image.

12. A device for monitoring a biofilm, the device comprising:
    a water tank configured to store water;
    a transparent monitoring substrate having a film thereon, and configured to be charged with positive charges on the film in order to form a biofilm on the transparent monitoring substrate;
    a light-emitting module located above the transparent monitoring substrate, and configured to emit light in the direction of the transparent monitoring substrate;
    an image sensor unit disposed under the transparent monitoring substrate, and configured to capture a shadow image of the biofilm formed on the transparent monitoring substrate; and
    a housing including
        an upper substrate to which the light-emitting module is fixed,
        sidewalls formed such that water is to pass therethrough, connected to the upper substrate, and configured to contain the transparent monitoring substrate, and
        a bottom substrate, where the image sensor unit is fixed, opposite to the upper substrate, and connected to the sidewalls,
    wherein the image sensor unit, the transparent monitoring substrate, and the light-emitting module are integrally formed, and
    wherein the film is made of at least one material of titanium oxide ($TiO_2$), aluminum oxide ($Al_2O_3$), and iron oxide ($Fe_2O_3$).

* * * * *